(12) United States Patent
Miller, III et al.

(10) Patent No.: US 11,355,910 B2
(45) Date of Patent: *Jun. 7, 2022

(54) SYSTEMS AND METHODS FOR DETECTING AND IDENTIFYING ARCING BASED ON NUMERICAL ANALYSIS

(71) Applicant: Hubbell Incorporated, Shelton, CT (US)

(72) Inventors: William Vernon Miller, III, Aldie, VA (US); Gary Michael Miller, Kearneysville, WV (US)

(73) Assignee: Hubbell Incorporated, Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/921,594

(22) Filed: Jul. 6, 2020

(65) Prior Publication Data

US 2020/0332948 A1 Oct. 22, 2020

Related U.S. Application Data

(63) Continuation of application No. 16/261,468, filed on Jan. 29, 2019, now Pat. No. 11,047,522, which is a
(Continued)

(51) Int. Cl.
*H02H 1/00* (2006.01)
*G01R 31/12* (2020.01)
(Continued)

(52) U.S. Cl.
CPC .......... *H02H 1/0015* (2013.01); *A47B 21/03* (2013.01); *A47B 21/0314* (2013.01);
(Continued)

(58) Field of Classification Search
None
See application file for complete search history.

(56) References Cited

U.S. PATENT DOCUMENTS

| | | |
|---|---|---|
| 5,047,724 A | 9/1991 | Boksiner et al. |
| 5,434,509 A | 7/1995 | Blades |

(Continued)

*Primary Examiner* — Tan T. Nguyen
(74) *Attorney, Agent, or Firm* — Dickinson Wright PLLC

(57) ABSTRACT

Method and system allowing more accurate detection and identification of unwanted arcing include novel processing of signal voltage representing recovered power-line current. In one implementation, arc-faults are detected based on numerical analysis where individual cycles of line voltage and current are observed and data collected during each cycle is processed to estimate likelihood of presence of arc-event within each individual cycle based on pre-defined number of arc-events occurring within pre-defined number of contiguous cycles. In another implementation, fast transient current spikes detection can be done by: computing difference values between consecutive line-current samples collected over a cycle, average of differences, and peak-to-peak value of line-current; comparing each difference value to average of difference; comparing each difference value to peak-to-peak value; and, based on calculation of composite of two comparisons, using thresholds to determine if arcing is present within processed cycle.

16 Claims, 18 Drawing Sheets

Related U.S. Application Data continuation of application No. 14/675,012, filed on Mar. 31, 2015, now Pat. No. 10,243,343, which is a continuation of application No. PCT/US2015/023414, filed on Mar. 30, 2015.

(60) Provisional application No. 61/973,251, filed on Mar. 31, 2014.

(51) Int. Cl.

| | | |
|---|---|---|
| *A47B 21/03* | (2006.01) | |
| *A61G 12/00* | (2006.01) | |
| *A61G 13/10* | (2006.01) | |
| *F16G 11/12* | (2006.01) | |
| *F16M 11/04* | (2006.01) | |
| *F16M 11/10* | (2006.01) | |
| *F16M 11/20* | (2006.01) | |
| *F16M 11/24* | (2006.01) | |
| *F16M 13/02* | (2006.01) | |
| *A61B 90/50* | (2016.01) | |
| *H01H 9/50* | (2006.01) | |
| *H01H 83/20* | (2006.01) | |

(52) U.S. Cl.
CPC ......... *A61G 12/004* (2013.01); *A61G 12/005* (2013.01); *A61G 13/107* (2013.01); *F16G 11/12* (2013.01); *F16M 11/046* (2013.01); *F16M 11/048* (2013.01); *F16M 11/10* (2013.01); *F16M 11/2014* (2013.01); *F16M 11/2021* (2013.01); *F16M 11/2064* (2013.01); *F16M 11/2092* (2013.01); *F16M 11/24* (2013.01); *F16M 13/02* (2013.01); *F16M 13/022* (2013.01); *G01R 31/1227* (2013.01); *H02H 1/0092* (2013.01); *A47B 2021/0321* (2013.01); *A61B 2090/506* (2016.02); *F16M 2200/021* (2013.01); *F16M 2200/041* (2013.01); *F16M 2200/048* (2013.01); *F16M 2200/06* (2013.01); *F16M 2200/063* (2013.01); *F16M 2200/065* (2013.01); *G01R 31/1272* (2013.01); *H01H 9/50* (2013.01); *H01H 2083/201* (2013.01)

(56) References Cited

U.S. PATENT DOCUMENTS

| | | | |
|---|---|---|---|
| 5,452,223 | A | 9/1995 | Zuercher et al. |
| 5,475,312 | A | 12/1995 | Sedding et al. |
| 5,485,093 | A | 1/1996 | Russell et al. |
| 5,659,453 | A | 8/1997 | Russell et al. |
| 5,729,145 | A | 3/1998 | Blades |
| 5,839,092 | A * | 11/1998 | Erger ............... G01R 31/52 702/58 |
| 5,963,406 | A | 10/1999 | Neiger et al. |
| 5,986,860 | A | 11/1999 | Scott |
| 6,088,205 | A | 7/2000 | Neiger et al. |
| 6,445,189 | B1 | 9/2002 | Pakonen et al. |
| 6,459,273 | B1 | 10/2002 | Dollar, II et al. |
| 6,839,208 | B2 | 1/2005 | MacBeth et al. |
| 7,062,388 | B2 | 6/2006 | Rivers et al. |
| 7,388,384 | B2 | 6/2008 | Kato et al. |
| 7,403,129 | B2 | 7/2008 | Zhou et al. |
| 7,579,843 | B2 | 8/2009 | Younsi et al. |
| 7,627,400 | B2 | 12/2009 | Dutoya et al. |
| 7,750,646 | B2 | 7/2010 | Maity et al. |
| 7,865,321 | B2 | 1/2011 | Muthu-Manivannan et al. |
| 8,457,910 | B2 | 6/2013 | Muthu-Manivannan et al. |
| 8,924,169 | B1 | 12/2014 | Ledenev |
| 10,243,343 | B2 * | 3/2019 | Miller, III ............ H02H 1/0015 |
| 10,707,670 | B2 * | 7/2020 | Miller, III ............ H02H 1/0092 |
| 2002/0008950 | A1 | 1/2002 | Kim et al. |
| 2003/0072113 | A1 | 4/2003 | Wong et al. |
| 2004/0252425 | A1 | 12/2004 | Baldwin et al. |
| 2006/0215335 | A1 | 9/2006 | Deshpande et al. |
| 2007/0058304 | A1 | 3/2007 | Parker et al. |
| 2007/0133134 | A1 | 6/2007 | Killroy et al. |
| 2008/0106832 | A1 | 5/2008 | Restrepo et al. |
| 2010/0097733 | A1 | 4/2010 | Tomimbang |
| 2010/0157486 | A1 | 6/2010 | Parker et al. |
| 2010/0169030 | A1 | 7/2010 | Parlos |
| 2010/0201371 | A1 | 8/2010 | Valcore et al. |
| 2011/0043214 | A1 | 2/2011 | Potter et al. |
| 2011/0249370 | A1 | 10/2011 | Nayak et al. |
| 2012/0112760 | A1 | 5/2012 | Yascovich et al. |
| 2013/0169290 | A1 | 7/2013 | Shea |
| 2013/0221973 | A1 | 8/2013 | Whisenand et al. |
| 2013/0226479 | A1 | 8/2013 | Grossjean |
| 2014/0168843 | A1 | 6/2014 | Privitera et al. |
| 2014/0278158 | A1 | 9/2014 | Miller |
| 2016/0187409 | A1 * | 6/2016 | Kolker ................. H02H 1/0015 361/42 |
| 2018/0115144 | A1 | 4/2018 | Murnane |

\* cited by examiner

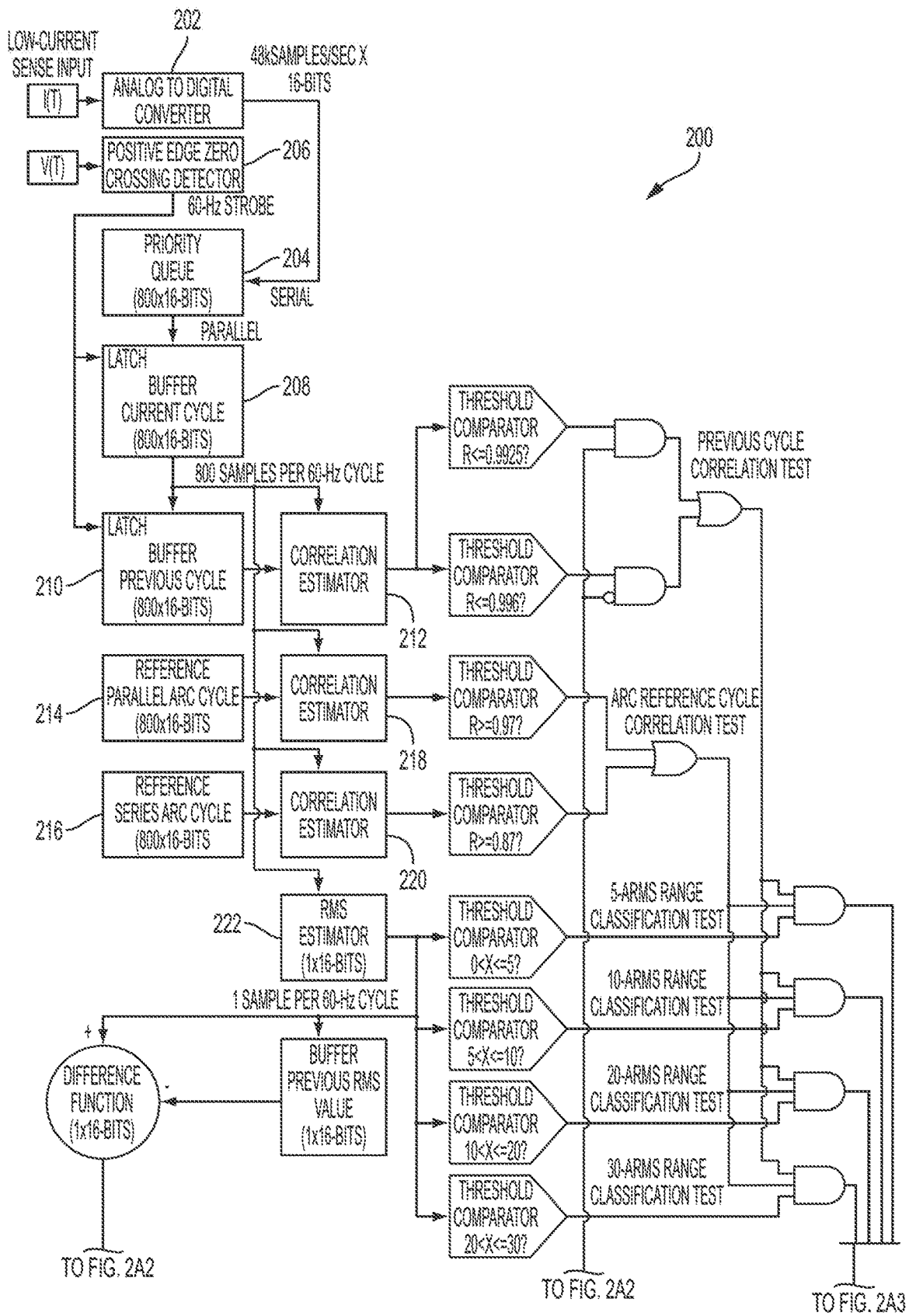
FIG. 2A1

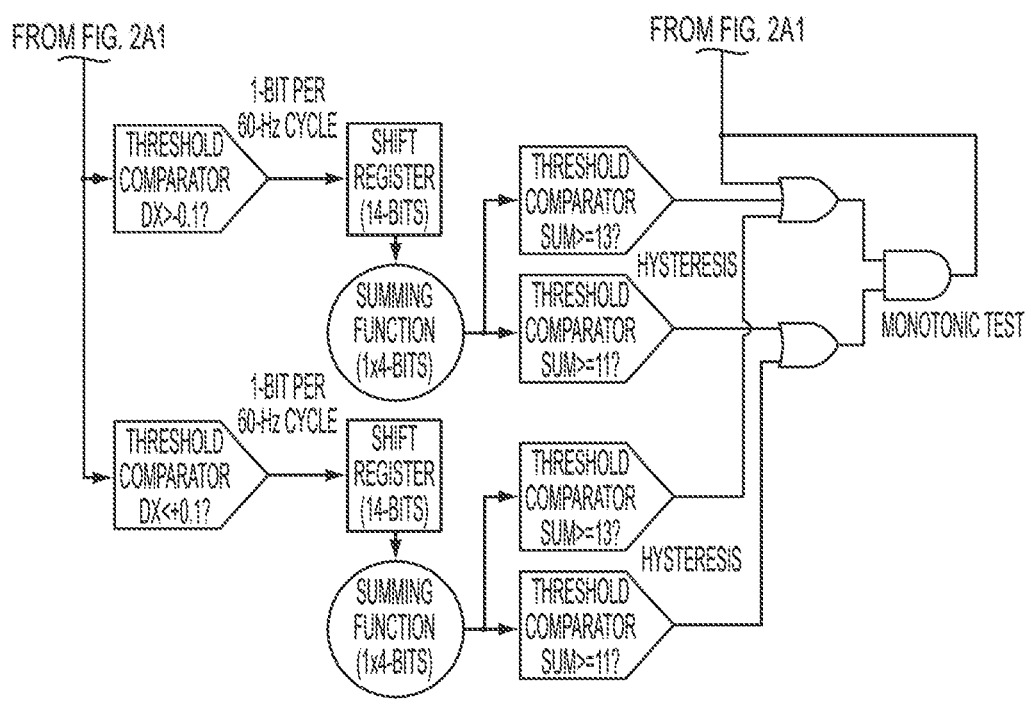
FIG. 2A2

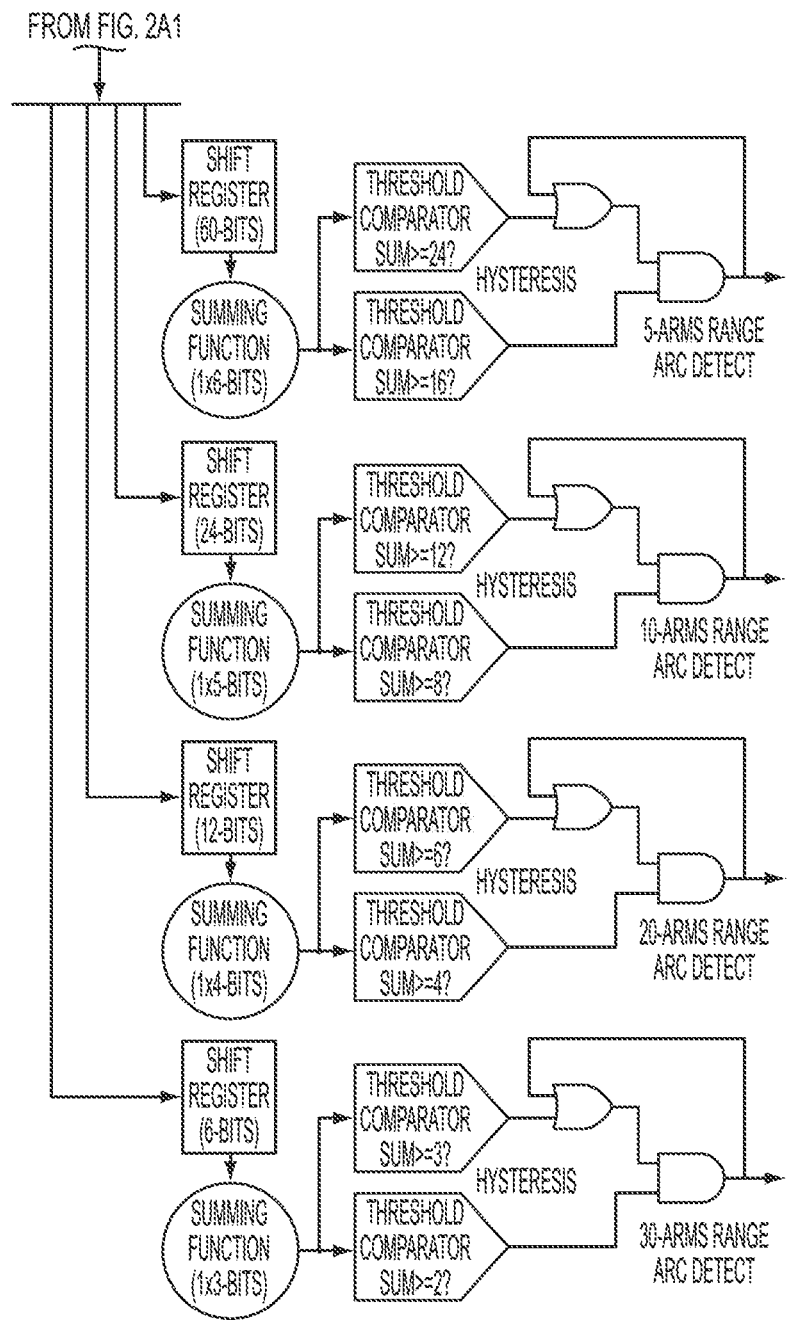
FIG. 2A3

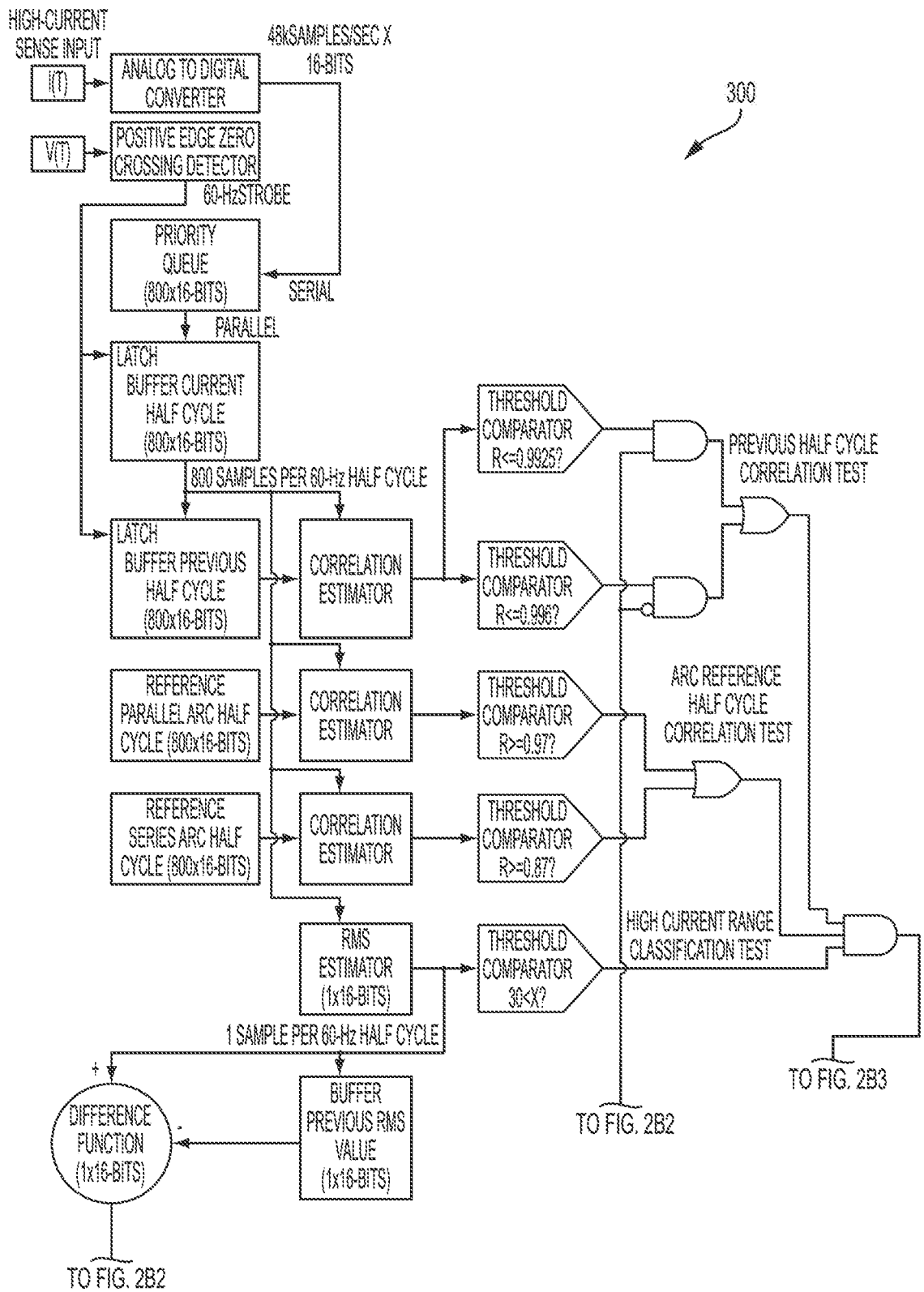
FIG. 2B1

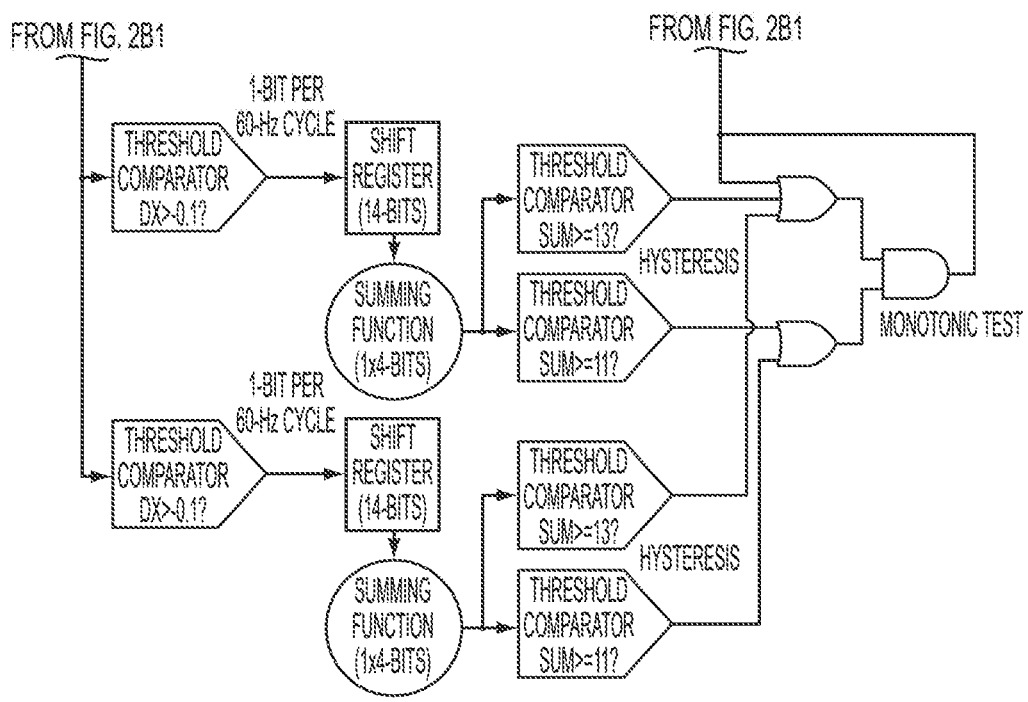
FIG. 2B2

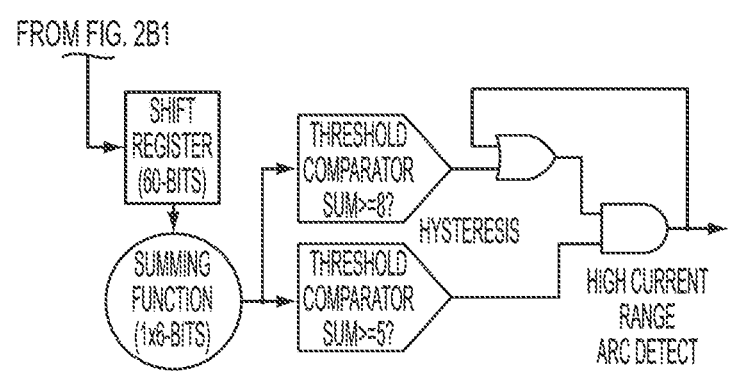
FIG. 2B3

SYSTEMS AND METHODS FOR DETECTING AND IDENTIFYING ARCING BASED ON NUMERICAL ANALYSIS

CROSS-REFERENCE TO RELATED APPLICATION

The present application is a continuation of U.S. Non-Provisional application Ser. No. 16/361,468, filed on Mar. 22, 2019, which is a continuation of U.S. of Non-Provisional application Ser. No. 14/675,012, filed on Mar. 31, 2015, which claims priority from U.S. Provisional Application No. 61/973,251, filed on Mar. 31, 2014, in the U.S. Patent and Trademark Office, and PCT/US/15/23414 filed Mar. 30, 2015. The present application relates to U.S. Provisional Application No. 61/781,553, filed on Mar. 14, 2013, in the U.S. Patent and Trademark Office, and to U.S. Non-Provisional application Ser. No. 14/206,093, filed on Mar. 12, 2014 the entire contents of which are hereby incorporated by reference.

FIELD OF THE INVENTION

The present application relates to the detection and identification of arcing, for example, for use with arc fault circuit interrupters.

BACKGROUND OF THE INVENTION

General Description of Arcing in Air and Solid Materials

Arcing can occur as a result of electrical wire damage. For example, a nail or a screw may puncture insulation or create a small break in a conductor. As a result, an arc can form, and traverse air or punch through compromised insulation. While all arcs are generally formed in similar ways, the electrical characteristics of arcing through air can be different from those of arcing through carbonized insulation.

An arc is an accelerated electron phenomenon. As an electric field increases, for example due to increasing voltage, electrons typically begin to move along the electric field, skipping from one atom to another. In a solid material, an electron flow over a finite amount of time can be considered a current. This current may be seen as an arc. Yet, when electrons are stripped from atoms at one end of a solid material, higher electric field strength is typically required to strip an additional electron. The arc path can as a result become unsuitable for sustaining an arc, forcing the arc to find another path. Over time, a used path can eventually recover, though several other arc paths may be used before a path or a portion of a path regains its suitability. In air, a similar phenomenon may occur. Yet, the movement of air can create additional features of a discharge. For example, "previous path" may not exist in the context of an arc in air, because of the movement of air. Furthermore, even when air is highly confined, it can be heated during arcing, resulting in substantial turbulence within the space.

Arcs in a solid material tend to break molecular bonds. They can encourage new bonds and new chemical composition in the solid material. In most plastics, for example, an arc can dissociate carbon from hydrogen. As hydrogen escapes into air, carbon is left in the plastic, usually with a black appearance, in a process often referred to as carbonization. Since carbon is more conductive than most plastics, areas of carbonization tend to be locations where arcing often recurs. These areas are usually in the form of small black pits, rather than large areas of carbon, which can nevertheless occur in extreme cases.

Although devices exist for detecting arcing in electrical circuits, they typically face such problems as oversensitive arcing detection or erroneous arcing identification. For example, conventional arc fault circuit interrupters often trip when detecting arcing due to the normal functioning of electrical components such as electric motors, rather than when detecting arcing due to electrical wire damage. Therefore, there is a need for a system that allows for more accurate detection and identification of potentially unwanted arcing with speed and accuracy appropriate for commercial applications.

SUMMARY OF THE INVENTION

Illustrative embodiments of the present invention address at least the above problems and/or disadvantages, and provide at least the advantages described below.

Exemplary embodiments of the present invention provide methods of detecting and identifying arcing generally based on numerical analysis where individual cycles of the line voltage and current are observed.

According to an exemplary embodiment of the present invention, zero-crossings on the rising edge of the voltage waveform are used to mark the beginning of each cycle for the line-current observations. The data collected during each cycle is subsequently processed to estimate the likelihood of the presence of an arc-event within each individual cycle. An arc-fault is determined to be present when a pre-defined number of arc-events are found to occur within a pre-defined number of contiguous cycles.

According to another exemplary embodiment of the present invention, methods and systems are provided where detection of fast transient current spikes can be done by computing difference function values for the line-current samples as they are collected over a single, for example 60-Hz, cycle, determine a maximum value and a minimum value of the plurality of line current samples for the cycle, calculating a peak-to-peak value of the line-current for the cycle as a relative difference between the maximum value and the minimum value of the plurality of line current samples, calculating an average of the difference function values, and comparing each of the difference function values to the calculated average of the difference function values and the calculated peak-to-peak value of the line-current for the cycle. According to an exemplary implementation of an embodiment of the present invention fast transient current spike in the cycle can be identified based on a result of at least one of such comparing.

According to yet another embodiment of the present invention, a product of the two comparisons can forms a composite spike detection function or a weighting function that emphasizes difference values that are large in comparison to both the peak-to-peak value of the line-current and the average difference of the line-current samples. In an exemplary implementation, the weighting function also de-emphasizes difference values that are small in comparison to both the peak-to-peak value of the line-current as well as the average difference of the line-current samples. The weighing function then aids in the identification of fast-transient current spikes within a single cycle of the line current by effectively improving the signal-to-noise ratio of the spike detector.

According to yet another embodiment of the present invention, based on the results of the composite comparison function calculation, thresholds can be used to determine if arcing is present within the processed cycle of current. In an exemplary implementation, two thresholds include a detection value limit threshold above which the result of the calculation for a given sample point is recognized as a current-spike, and a minimum count threshold setting a minimum required number of sample points within the cycle for which the result of the calculation exceeds the defined current-spike detection value limit. According to an exemplary implementation, a reliable determination of the presence of arcing within a given cycle may then be made through the proper adjustment of both the detection value limit and minimum count thresholds

BRIEF DESCRIPTION OF THE DRAWINGS

The above and other exemplary features, aspects and advantages of the present invention will become more apparent from the following detailed description of certain exemplary embodiments thereof when taken in conjunction with the accompanying drawings in which:

FIGS. 2A1, 2A2, and 2A3 show an illustrative method of detecting and identifying arcing according to an exemplary embodiment of the present invention;

FIGS. 2B1, 2B2, and 2B3 show an illustrative method of detecting and identifying arcing according to another exemplary embodiment of the present invention; and FIG. 3 shows an illustrative example of line-current cycles in which arcing is both present and absent.

DETAILED DESCRIPTION OF ILLUSTRATIVE EMBODIMENTS

Figure 1:
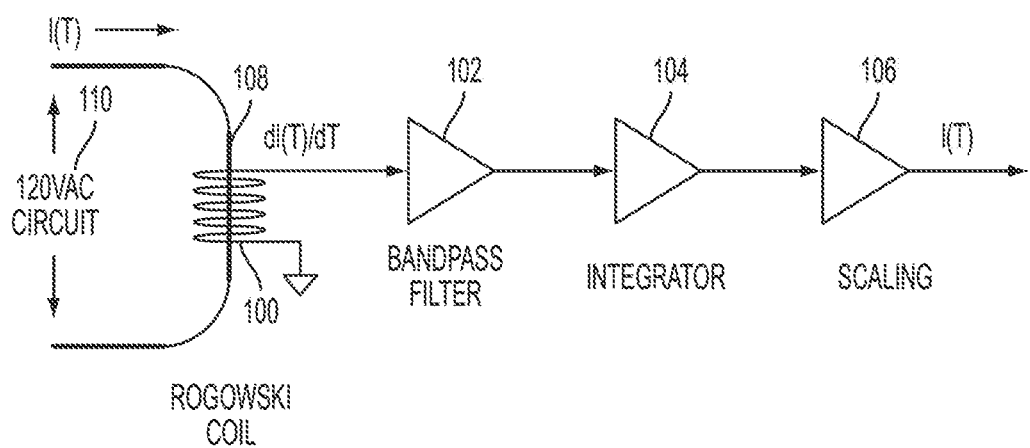
FIG. 1 illustrates a block diagram of a circuit for performing power-line current monitoring and analog pre-processing according to an exemplary embodiment of the present invention.
Figure 3:
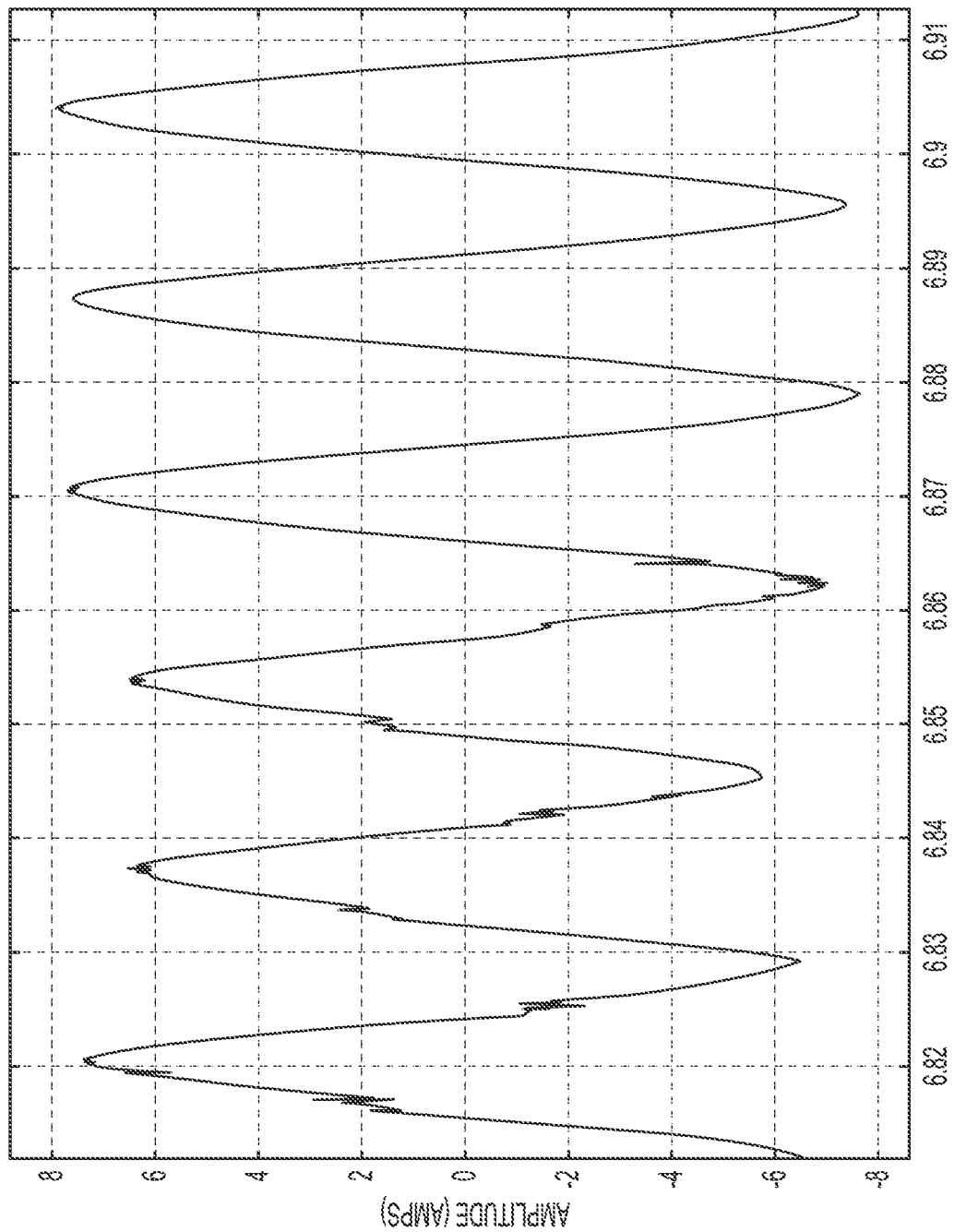

This description is provided to assist with a comprehensive understanding of illustrative embodiments of the present invention described with reference to the accompanying drawing figures. Accordingly, those of ordinary skill in the art will recognize that various changes and modifications of the illustrative embodiments described herein can be made without departing from the scope and spirit of the present invention. Also, descriptions of well-known functions and constructions are omitted for clarity and conciseness. Likewise, certain naming conventions, labels and terms as used in the context of the present disclosure are, as would be understood by skilled artisans, non-limiting and provided only for illustrative purposes to facilitate understanding of certain illustrative implementations of the embodiments of the present invention.

Generally referring to FIGS. 1-11, systems and methods can detect and identify or assist in the detection and identification of arcing.

According to an illustrative embodiment of the present invention, individual cycles of the line voltage and current are observed, and a likelihood of the presence of an arc-event within an individual cycle is estimated based upon the following criteria:

(1) Correlation of each observed cycle of the current waveform with a known arc reference cycle.
(2) Correlation of each observed cycle of the current waveform with the preceding observed cycle.
(3) Determination of monotonic behavior in the RMS amplitude of the line-current from observations of the current waveform over a pre-determined number of cycles.

According to an illustrative embodiment of the present invention, individual cycles of the line voltage and current are observed with reference to zero-crossings on the rising edge of the voltage waveform which are used to mark the beginning of each cycle for the line-current. The data collected during each cycle can be subsequently processed to estimate the likelihood of the presence of an arc-event within each individual cycle. For example, an arc-fault is determined to be present when a pre-defined number of arc-events are found to occur within a pre-defined number of contiguous cycles.

In an illustrative embodiments of the present invention, using first (1) criterion, a single known arc reference cycle is produced through observation of the current while arc events are generated in a controlled fashion under a multitude of conditions, for example such as those specified in Standards documents such as UL1699. The known arc reference cycle can be determined from the observations as the normalized average expected wave-shape of a single cycle of current in which an arc is present. Observations of the line current cycle are correlated with the known arc reference in order to estimate the likelihood that an arc-event is present within the observed cycle.

In general, current waveform produced by some electrical equipment, such as for example an electronic lamp dimmer controlling an incandescent light-bulb, can mimic a signature waveform of an arc-event. The observed current from these types of loads can be well correlated with the known arc reference cycle described for the first (1) criteria and can produce a false indication of the presence of an arc-event.

According to an exemplary embodiment of the present invention, in order to distinguish the current cycles produced by these types of loads from cycles in which an actual arc-event is present, the second (2) criteria correlates an observed cycle of the line current with the preceding observed cycle. Relative to a true arc-fault condition, electrical loads that mimic the signature waveform of an arc-event produce a current waveform that is more uniform on a cycle-to-cycle basis when observed over multiple cycles. To the contrary, under a true arc-fault condition the resulting current waveform is more random on a cycle-to-cycle basis. The second (2) criterion then estimates the likelihood that an arc-event identified by the first criteria is actually an electrical load that mimics the signature waveform of an arc-event.

There are still other types of electrical equipment that can produce a current waveform that mimics the signature waveform of an arc-event, and for which a given set of cycles will not be well correlated with their predecessors when observed over multiple cycles. This type of behavior can be observed when the load presented by the equipment varies over time, for example as is the case with a variable speed drill. Furthermore, it can be observed that these types of varying loads generally produce a monotonic behavior in the root-mean-square (RMS) amplitude of the line current when observed over a pre-determined number of cycles. To the contrary, the current waveform produced under a true arc-fault condition is generally not monotonic due to the more random nature of the arc-events that occur during contiguous observations of the line-current.

According to an exemplary embodiment of the present invention, an outcome of the third (3) criterion can be used to adjust the detection thresholds of the first two, (1) and (2), criteria in order to facilitate prevention of false detection of an arc-fault under a varying load condition on the line.

According to an exemplary embodiment of the present invention, an arc-event is determined to be present when a specific combination of outcomes occurs in the aforementioned three criteria, (1), (2) and (3), following observation of a single cycle of the current waveform. In an exemplary implementation, an arc-event is determined to be present during the cycle when the observations of the current are well correlated to the known arc reference cycle, and are not well correlated to the observations taken during the preceding cycle.

In an exemplary implementation of the embodiments of the present invention, thresholds that are used to gauge the degree of correlation required for arc-event detection can be specified based upon the determination of monotonic behavior in the RMS amplitude of the line-current following observations of the current waveform over a pre-determined number of cycles In an exemplary implementation, an arc-fault can be determined to be present when a pre-defined number of arc-events are found to occur within a pre-defined number of contiguous cycles. Both the required number of detected arc-events and the number of cycles in the observation window are determined based on a range classification of the RMS amplitude of each observed cycle of the line-current. For example, range classifications may be extracted from Standards documents such as UL1699 which specifies different arc test clearing times based on the current level being tested, where for example ranges of 0<x<=5 Arms, 5<x<=10 Arms, 10<x<20 Arms and 20<x<=30 Arms are specified for an 20 Amp AFCl.

According to an exemplary embodiment of the present invention a sensed current can be processed by electronics of FIG. 1 where current I(t) is passed through a sensor coil and analog electronics, including for example, a band-pass filter, an integrator circuit and a scaling circuit, that condition the sensed current signal prior to handing it off via an analog to digital converter to, for example a microprocessor executing a detection algorithm.

As illustrated in the example of FIG. 1, power line-current can be monitored via an air-core Rogowski coil 100 attached around the hot lead 108 of an AC circuit 110. The coil produces a voltage that is proportional to the time-derivative of the current flowing in the AC circuit. In an exemplary implementation, the signal voltage from the coil is band-pass filtered by a band-pass filter circuit 102 and integrated by an integrator circuit 104 in order to recover a signal voltage that is proportional to the current flowing in the AC circuit. In an exemplary implementation, band-pass filter 102, with a 3-dB pass-band between 1-Hz and 8-kHz, attenuates unnecessary low- and high-frequency content that might otherwise saturate the integrator 104. In yet another exemplary implementation, a gain stage 106 then scales the signal to the full-scale input voltage of the Analog-to-Digital (A/D) converter which will sample the signal for subsequent digital post-processing. For example, a 30-Arms line-current may be scaled to a full-scale voltage of 3.0 Vdc at the A/D converter.

According to an exemplary embodiment of the present invention, signal voltage representing the recovered power-line current can be processed for arc-detection as conceptually illustrated in FIGS. 2A1, 2A2, 2A3 and 2B1, 2B2, 2B3. In an exemplary implementation, requirements for the response to and the conditions for recognition of an arc can be obtained from UL standard 1699. For example, the time in which the AFCl has to interrupt the circuit upon detection of an arc under the various conditions outlined in UL1699 is dependent upon the RMS amplitude of the line-current present at the time the arc is detected. In an exemplary implementation, pursuant to the standard, currents up to 500-Arms are specified in the conformance tests for certification. In order to preserve the resolution for currents at or below 150% of the 20-Amp current rating of the AFCl while at the same time maintaining the ability to handle a 500-Arms full-scale requirement with the available dynamic range of the 16-bit A/D converter, it is necessary to divide and appropriately scale the monitored current into low- and high-ranges. FIGS. 2A1, 2A2, and 2A3 provide a process flow and component diagram 200 according to an exemplary implementation depicting a UL1699 standard driven arc detection algorithm for currents at or below 30-Arms. FIGS. 2B1, 2B2, and 2B3 (where labels for like elements have been omitted for conciseness) provide a process flow and component diagram 300 according to an exemplary implementation for currents up to 500-Arms. In a further exemplary implementation, the UL1699 standard specifies the recognition of arcs within half-cycles of the line-current for the conditions in which the high-range detection process shown in FIGS. 2B1, 2B2, and 2B3 applies, whereas full-cycles of the line-current are evaluated in the recognition of arcs in the low-range of FIGS. 2A1, 2A2, and 2A3.

According to an exemplary implementation, as shown in FIGS. 2A1, 2A2, and 2A3 for low-range line-currents, the signal voltage representing the recovered power-line current is first sampled by an A/D converter 202 which produces 16-bit samples at a rate of 48-kSamples/sec. The samples are then passed into a priority queue 204. The power-line voltage is also monitored for positive-edge zero-crossings in the voltage waveform. Output of a zero-crossing detector circuit 206 marks the beginning of each 60-Hz cycle and is used to synchronize processing of the line-current samples, thereby preserving the relative phase relationship between the monitored line-current and line-voltage on a cycle-to-cycle basis. Samples of the line-current are stored sequentially in the priority queue 204, beginning with the first sample taken following the detection of a zero-crossing event in the line-voltage and ending with the last sample taken prior to the next zero crossing event. The contents of the priority queue represent the most recent cycle of the observed line current and are latched within a buffer 208 upon detection of the zero-crossing event in the line voltage. The present contents of the buffer 208 are transferred to RMS Estimator 222. Similarly, the present contents of the buffer 208 are also transferred to a second buffer 210 such that the contents of the second buffer represent the previous cycle of observed line-current.

Exemplary embodiments of the present invention include inter-cycle correlation where the contents of buffers containing samples of the most recent and previous cycles of observed line-current are compared via correlation by, for example, a correlation estimator 212. The current flow during an arc-event is expected to be more random than the current flow under normal operating conditions. For example, under normal operating steady-state conditions the current waveform is expected to exhibit more uniformity from one cycle to the next than may be observed during an arc-event. Hence, it is expected that the contents of the buffers 208 and 210 representing the most recent and previous observations of the line-current will have a higher degree of correlation on average when arcing is not present than when arcing is present. This property is illustrated in the example FIG. 3 which shows captured line-current in which arcing is present during the first three cycles and absent in the last three.

In an exemplary implementation, correlation between the two sets of data X and Y can be expressed as the normalized correlation coefficient R(X,Y) as determined from the following equation, $$R(X, Y) = \frac{C(X, Y)}{\sqrt{C(X, X)C(Y, Y)}}$$

where:
X is the set of data samples representing the most recent observed cycle of the line-current,
Y is the set of data samples representing the previous observed cycle of the line-current,
C(X,Y) is the unbiased estimate of sample covariance between variables X and Y.
C(X,X) is the unbiased estimate of sample covariance of variable X, and
C(Y,Y) is the unbiased estimate of sample covariance of variable Y.

The unbiased estimates of sample covariance for variables X and Y are determined from the equations, $$C(X, Y) = \frac{1}{N-1} \sum_{k=1}^{N} (X(k) - \overline{X})(Y(k) - \overline{Y})$$

$$C(X, X) = \frac{1}{N-1} \sum_{k=1}^{N} (X(k) - \overline{X})^2$$

$$C(Y, Y) = \frac{1}{N-1} \sum_{k=1}^{N} (Y(k) - \overline{Y})^2$$

where,
X(k) is the kth sample of variable X,
$\overline{X}$ is the expected value of variable X,
Y(k) is the kth sample of variable Y,
$\overline{Y}$ is the expected value of variable Y, and
N is the minimum of the number of samples taken for variables X and Y.

Figure 4:
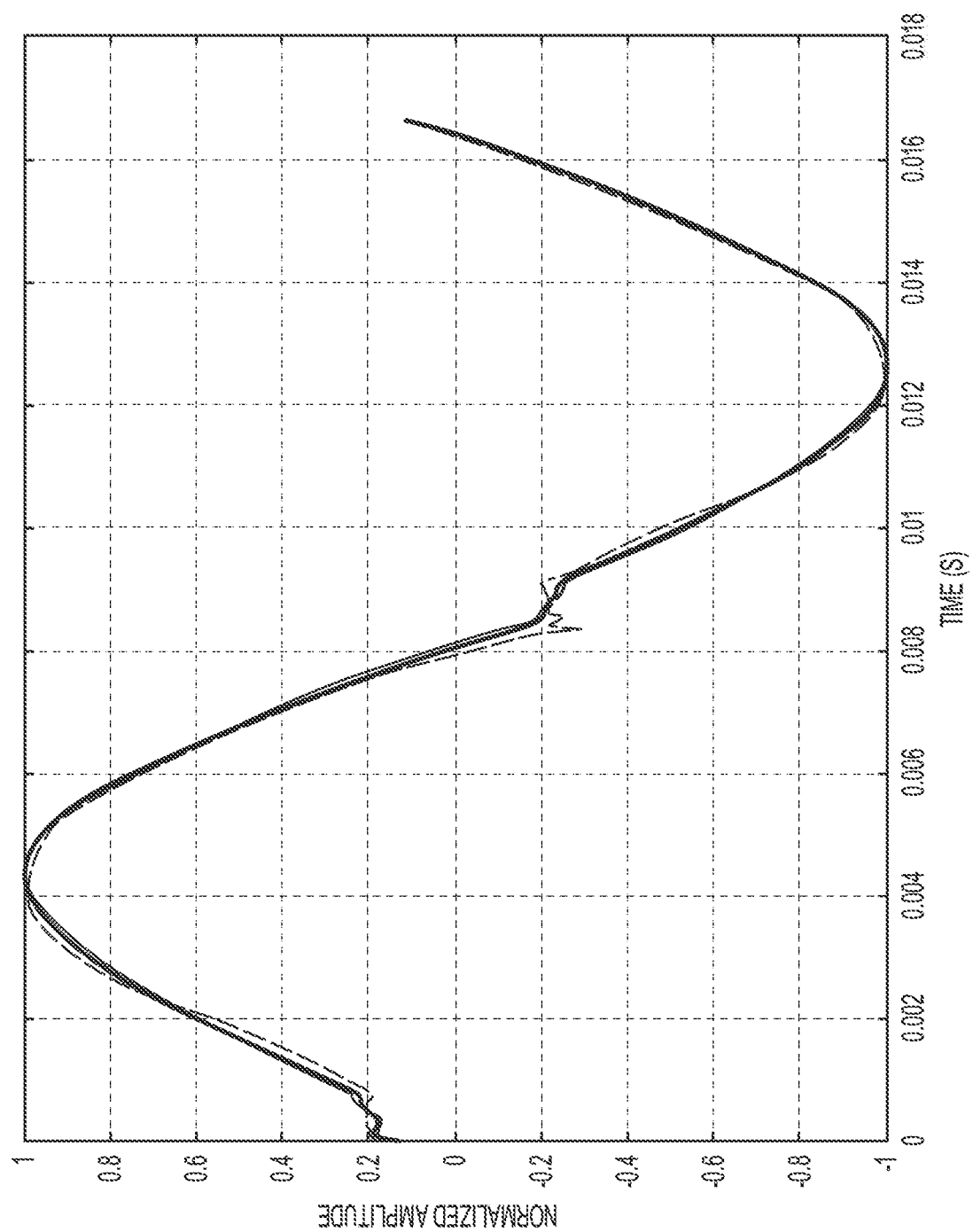
FIG. 4 shows an illustrative example of a series arc reference waveform according to an exemplary implementation of the present invention.
Figure 5:
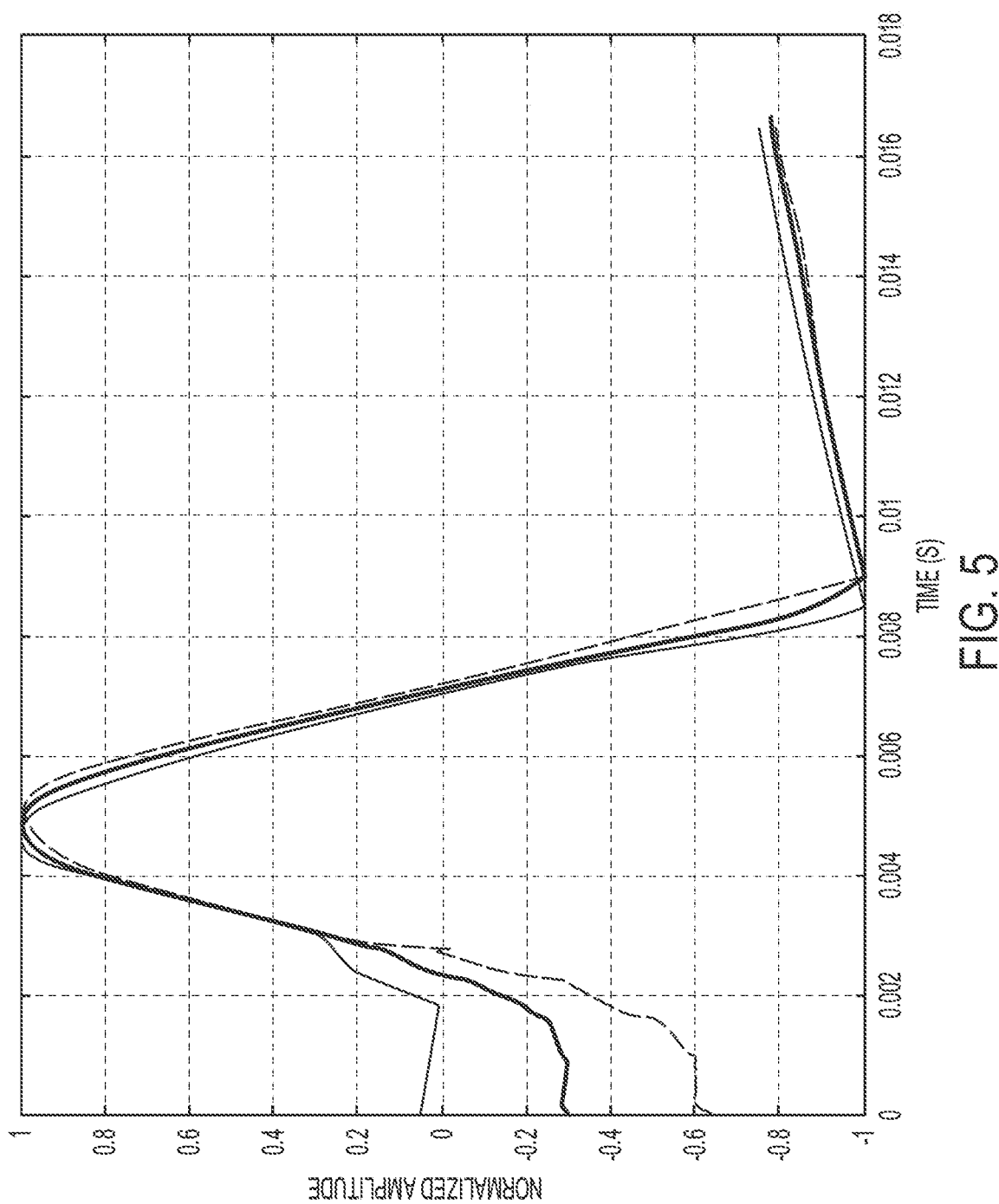
FIG. 5 shows an illustrative example of an arcing half-cycle reference waveform according to an exemplary implementation of the present invention.

According to exemplary embodiments of the present invention, arc references 214, 216 can be provided as follows. The contents of the buffer containing the samples of the most recent cycle of the line-current can be also compared via correlation 218, 202 to multiple sets of reference data that represent a typical cycle of current with an arc present. The sets of arc reference cycle data represent arcing that occurs under various conditions, and can be derived empirically from measurement data taken while performing tests, for example as described in UL Standard 1699. Collected data can be reviewed on a cycle-by-cycle basis and cycles in which arcing is present can be tagged. Each arc reference cycle can then be generated as the composite mean of the tagged cycles. Examples of arc reference cycles are shown in FIGS. 4 and 5.

Figure 6:
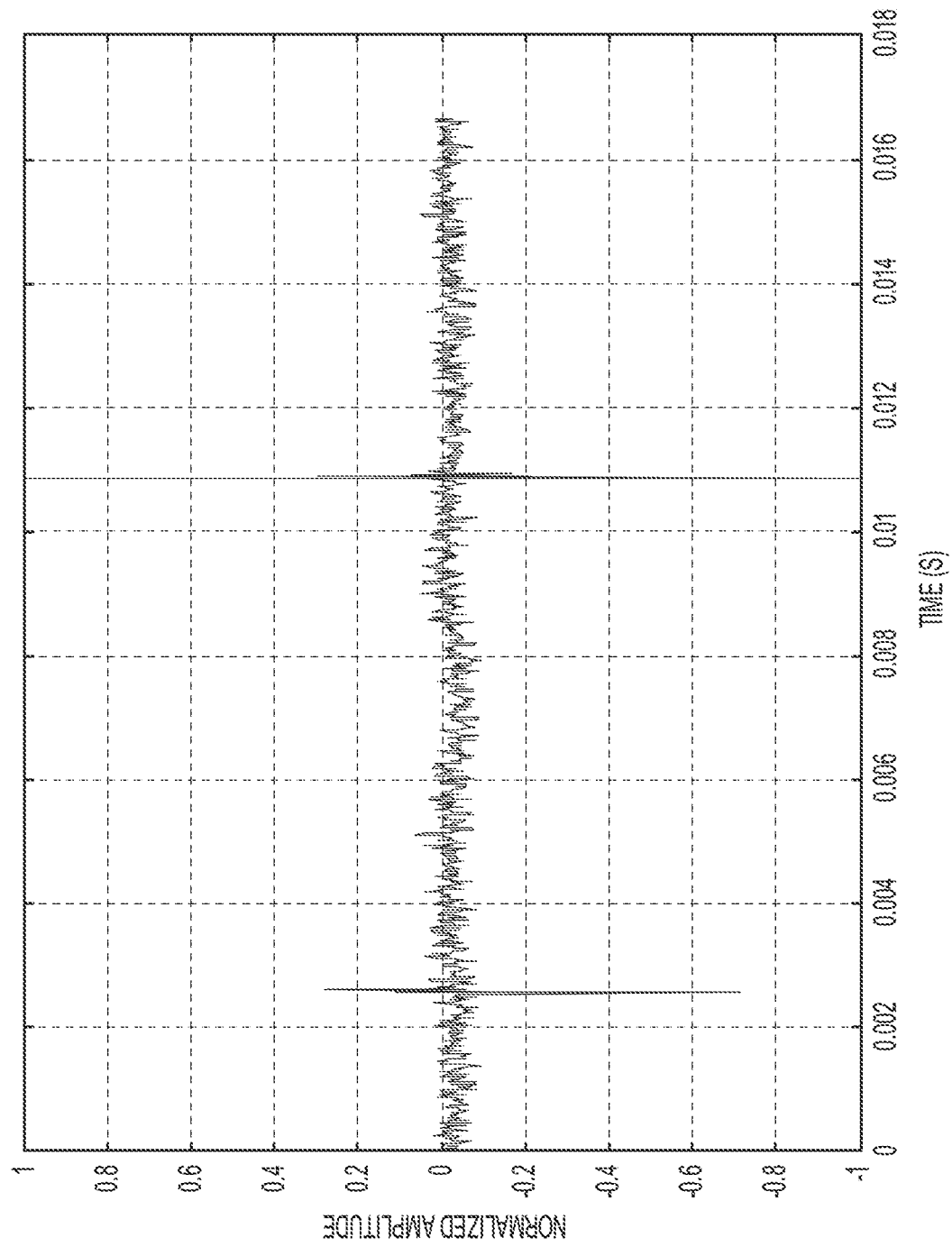
FIG. 6 shows an illustrative example of a waveform representative of a fast transient arcing phenomenon.
Figure 7:
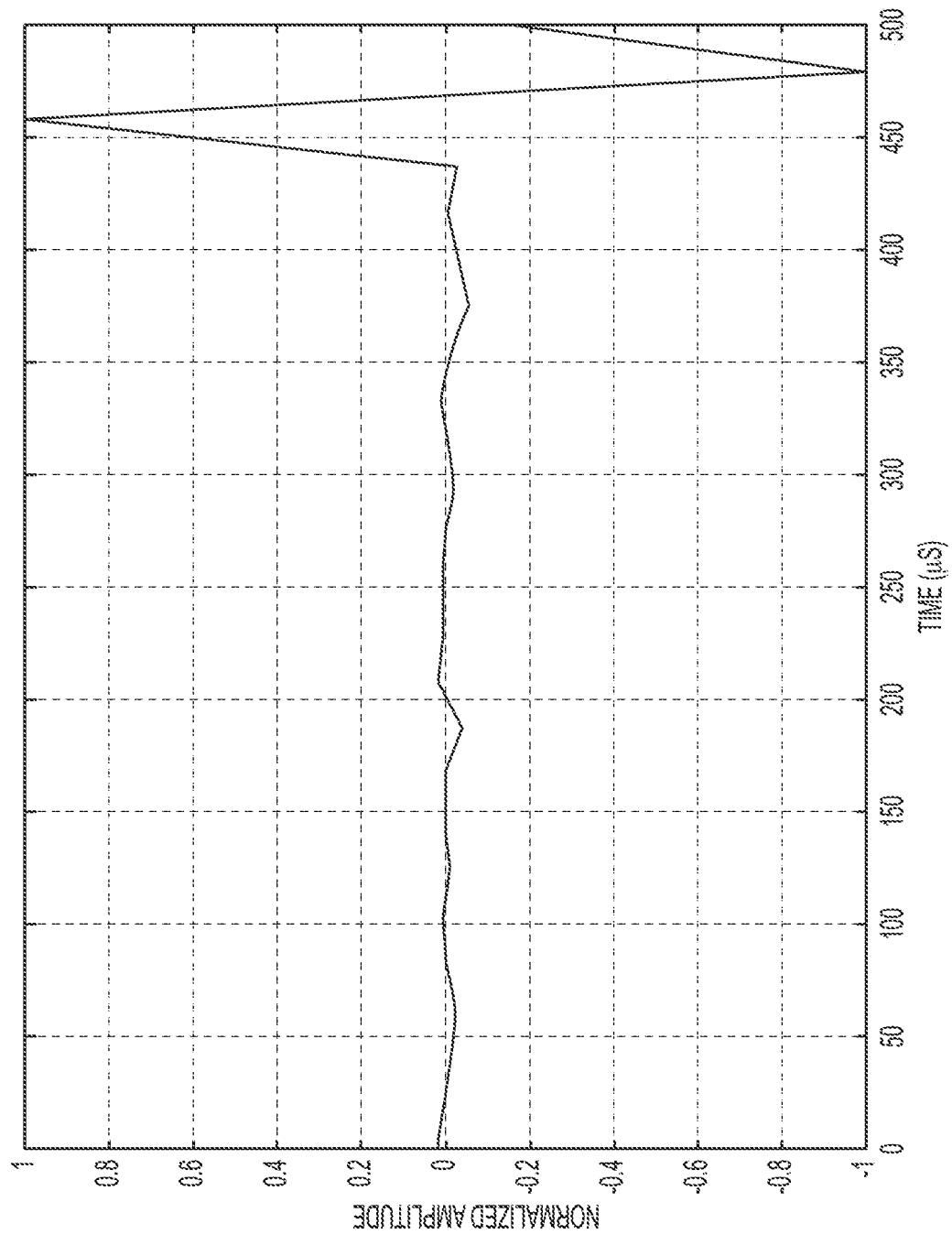
FIG. 7 shows an illustrative example of a fast transient arc pulse reference waveform according to an exemplary implementation of the present invention.
Figure 8:
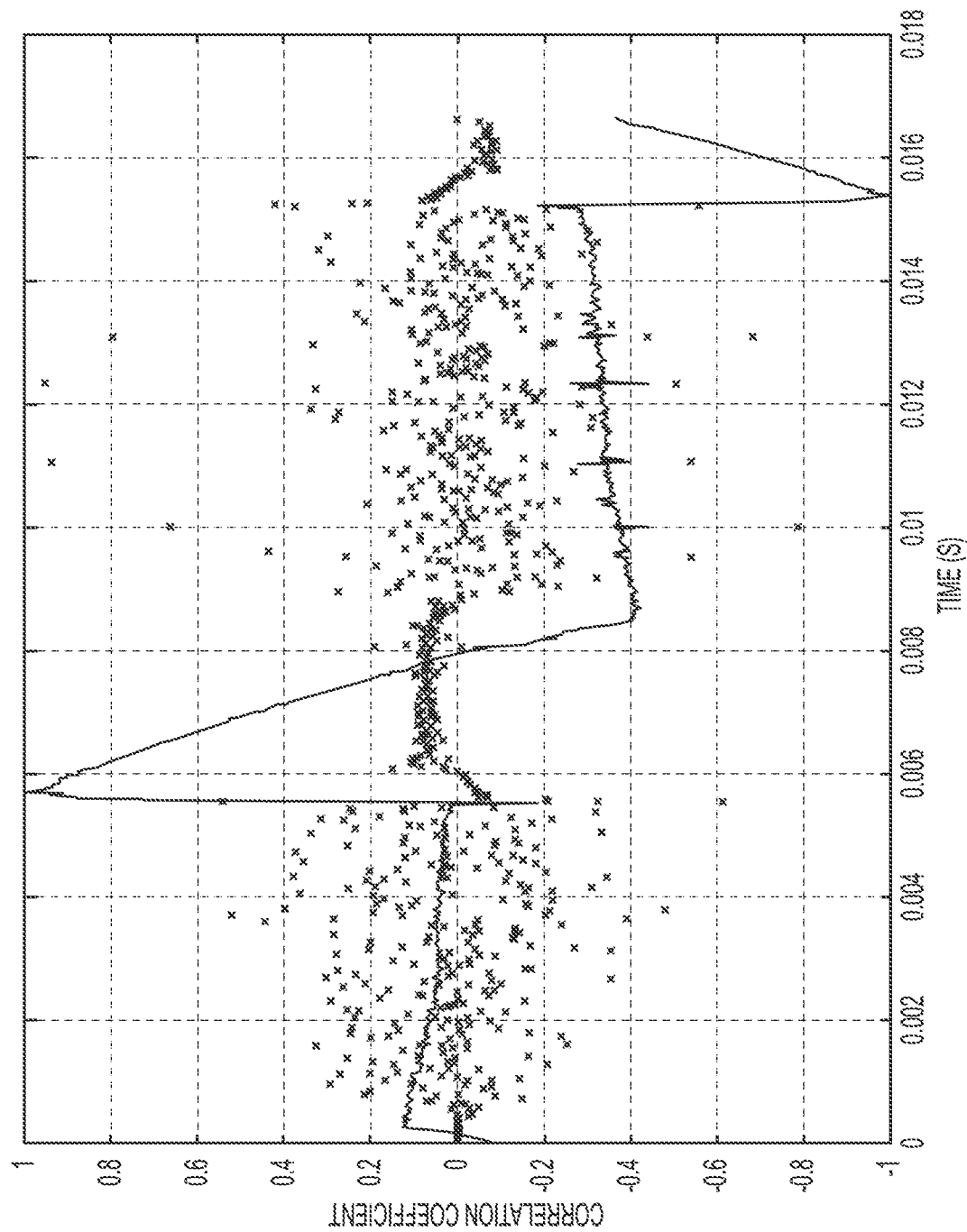
FIG. 8 shows an illustrative example of results of a correlation between line-current and arc-pulse reference according to an exemplary implementation of the present invention.

According to an exemplary implementation, another observable phenomenon in the presence of arcing can be manifested by random appearance of fast transient current spikes, an example of which is shown in FIG. 6. An example of an arc reference representing such behavior is shown in FIG. 7, which was arrived at through observation and empirical analysis of data taken while performing tests as described in UL Standard 1699. Samples of the line-current can be correlated with such an arc-pulse reference once every sampling interval. An example of the results of the per-sample correlation of the line-current data with the arc-pulse reference is shown in FIG. 8 where the line-current is plotted as a continuous line and the "x" markings indicate the correlation coefficient value for each sample interval.

Figure 9:
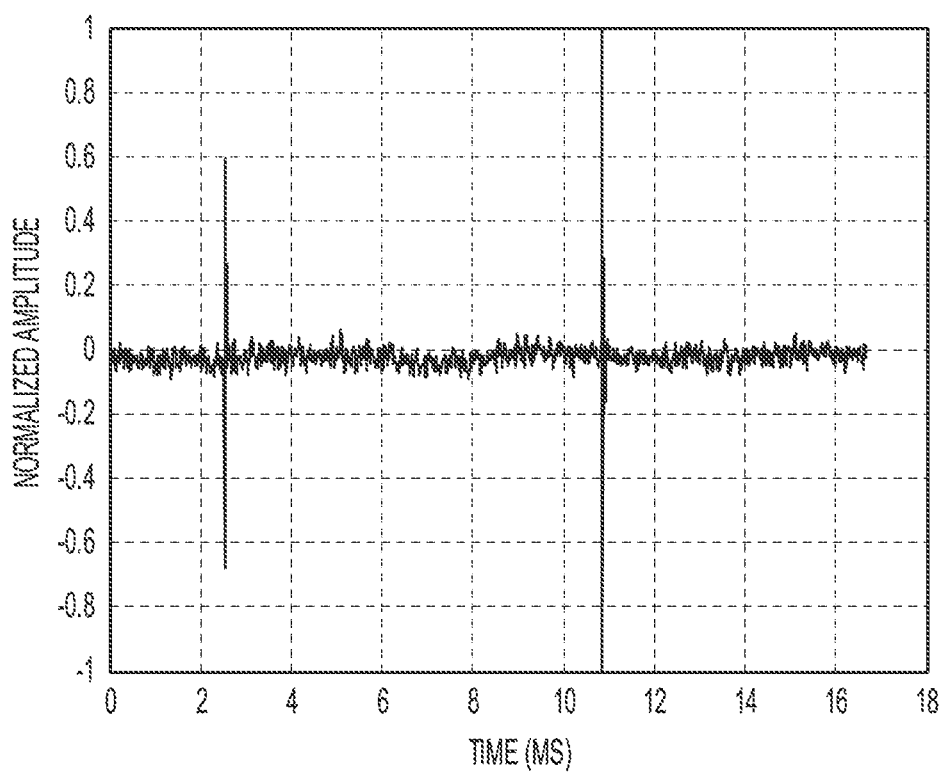
FIG. 9 shows another illustrative example of a waveform representative of a fast transient arcing phenomenon.

FIG. 9 illustrates another example of random appearance of fast transient current spikes as an observable phenomenon in the presence of arcing.

According to another exemplary embodiment of the present invention, detection of fast transient current spikes can be done by first computing a difference function for the line-current samples as they are collected over a single 60-Hz cycle. For example, each entry for the difference function is calculated by subtracting the value of the previous line-current sample from the current one. The maximum and minimum values of the line-current are also determined as the samples are collected, such that the peak-to-peak value of the line-current for the cycle can be calculated as their relative difference. The average of the difference function values is then determined at the end of the cycle, and each of the difference function values is compared to both the calculated average difference value and to the peak-to-peak value of the line-current during the cycle. The two comparison operations are defined by the equations:

$$S_1(X_n) = \frac{|X_n - X_{(n-1)}|}{[\max(X) - \min(X)]}$$

$$S_2(X_n) = \frac{|X_n - X_{(n-1)}|}{\left(\frac{1}{N-1}\right)\sum_{k=2}^{N}(|X_k - X_{(k-1)}|)}$$

where,
$S_1(X_n)$ is the comparison result of the nth difference value to the peak-to-peak value of the line-current,
$S_2(X_n)$ is the comparison result of the nth difference value to the average difference value,
$X_n$ is the nth sample of the collected line-current data X,
$X_{(n-1)}$ is the sample preceding the nth sample of the collected line-current data X,
max(X) is the maximum value of the line-current samples collected during the single 60-Hz cycle,
min(X) is the minimum value of the line-current samples collected during the single 60-Hz cycle, N is the number of line-current samples collected during the single 60-Hz cycle.

The product of the two comparisons forms a composite spike detection function defined by the equation, $$S_3(X_n)=S_1(X_n)*S_2(X_n)$$

Figure 10A:
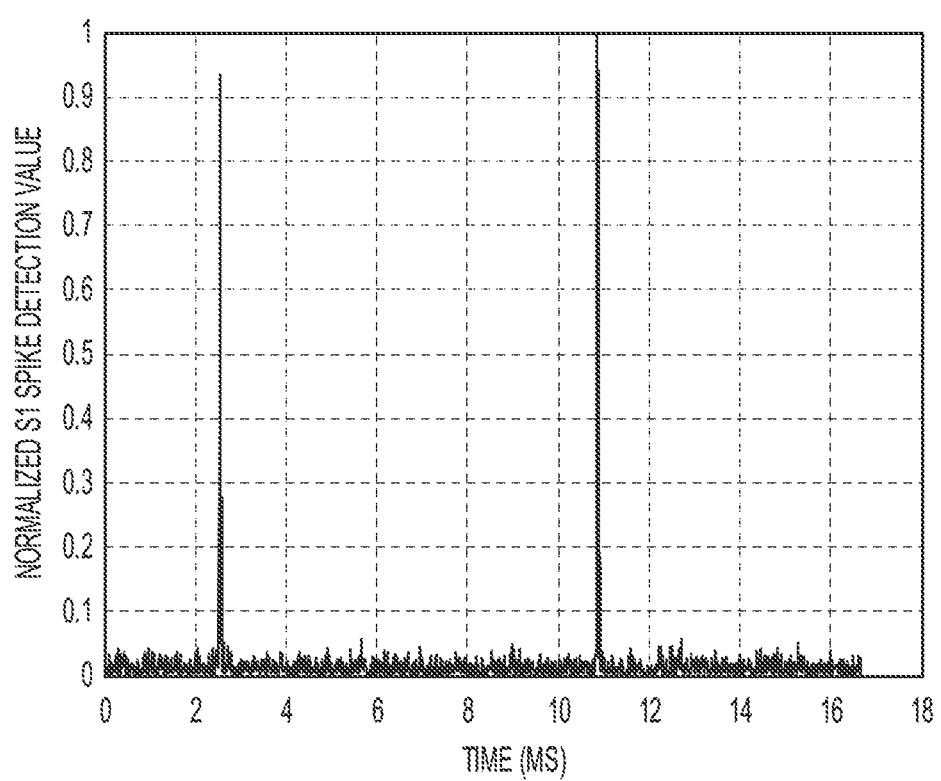
FIGS. 10A, 10B, and 10C show a graphic representation of analyses performed according to an exemplary embodiment of the present invention in the identification of fast-transient current spikes within a single cycle of the line current.
Figure 10B:
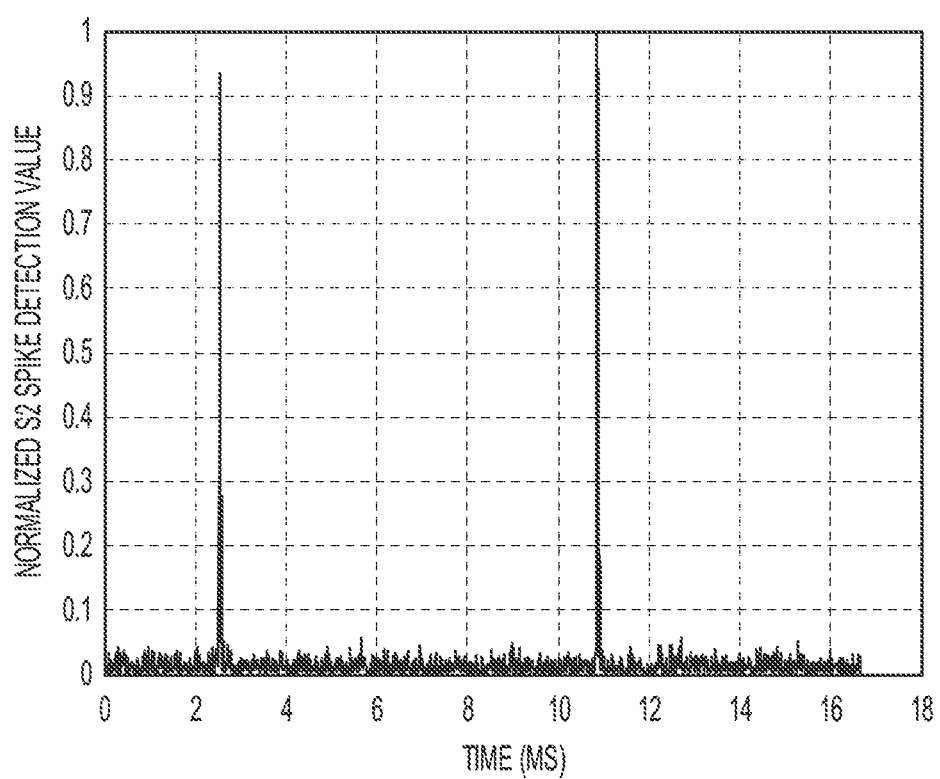
Figure 10C:
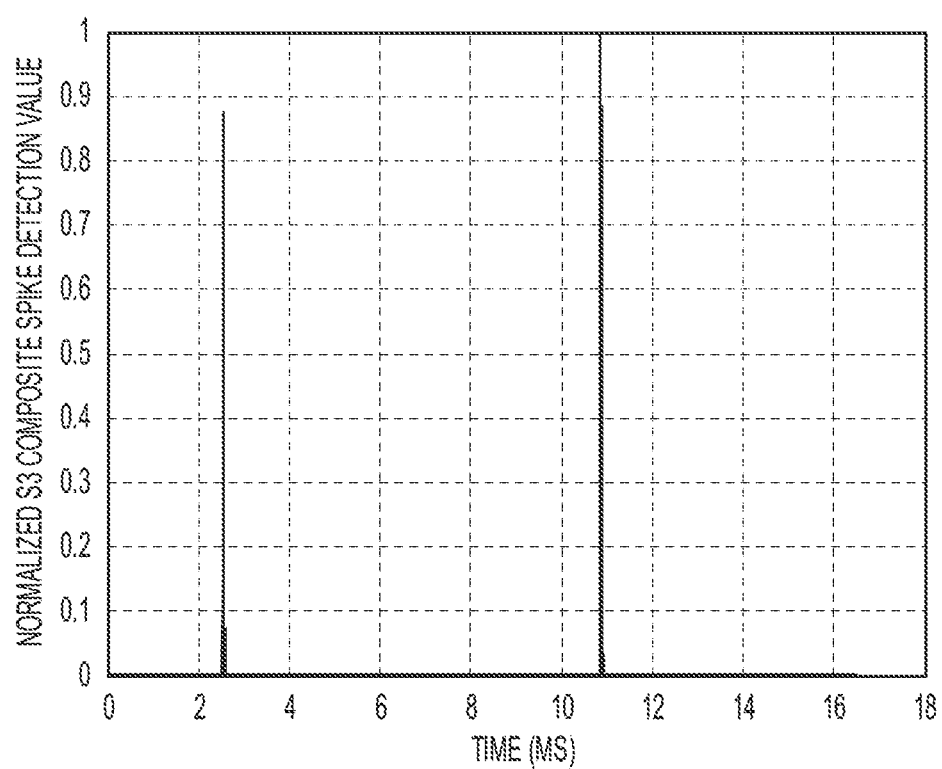

While either S1 or S2 could be used to identify fast transient current spikes, their composite forms a weighting function that emphasizes difference values that are large in comparison to both the peak-to-peak value of the line-current and the average difference of the line-current samples. Likewise, the weighting function de-emphasizes difference values that are small in comparison to both the peak-to-peak value of the line-current as well as the average difference of the line-current samples. The weighing function then aids in the identification of fast-transient current spikes within a single cycle of the line current by effectively improving the signal-to-noise ratio of the spike detector. The effect is illustrated in FIGS. 10A, 10B, and 10C, in which the normalized results of the comparison calculations for S1, S2, and S3 are shown respectively for the fast-transient current spike data shown in FIG. 9.

Figure 11:
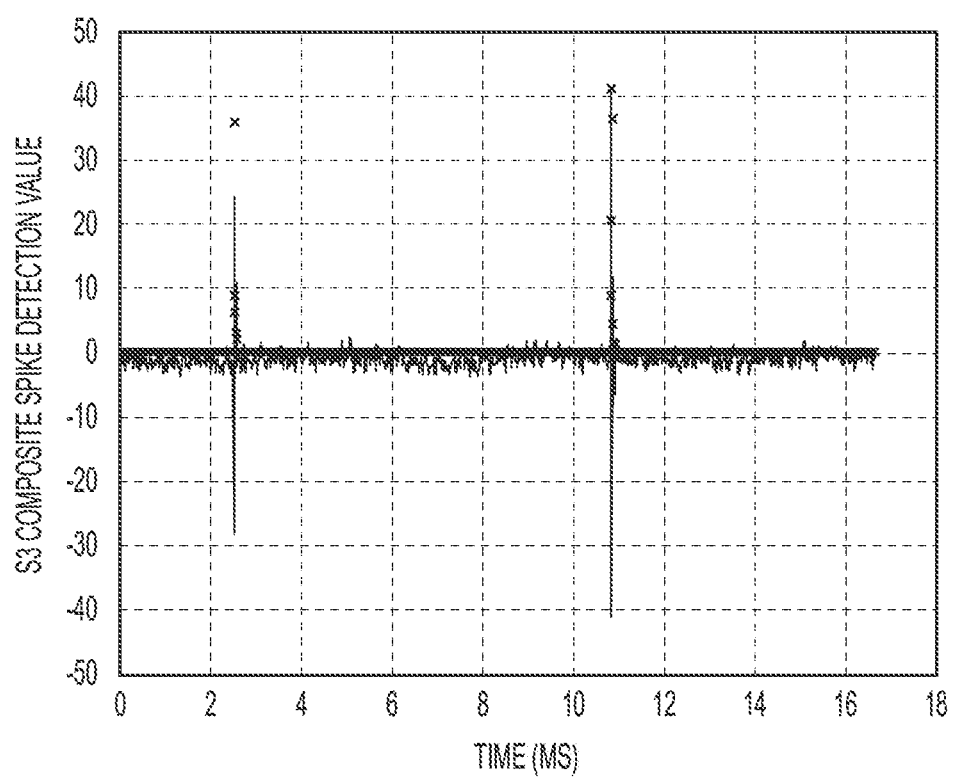
FIG. 11 illustrates results of calculations at each sample according to an exemplary embodiment of the present invention.

The un-scaled result of the S3 composite comparison calculation for the fast-transient data in FIG. 9 is shown in FIG. 11, with the "x" markings indicating the result of the calculation at each sample point (note that the majority of the "x" markings when plotted appear as a thick horizontal line extending along the Time axis at essentially zero of Detection Value axis). For further illustration, in FIG. 11 the line-current is plotted as a continuous solid line and is scaled to the limits of the calculated S3 comparison values over the cycle for illustrative purposes.

Based on the results of the S3 composite comparison function calculation, thresholds can be used to determine if arcing is present within the processed cycle of current. According to an exemplary implementation, two thresholds would be required: one marking the detection value limit above which the result of the calculation for a given sample point is recognized as a current-spike, and another defining the minimum required number of sample points within the cycle for which the result of the calculation exceeds the defined current-spike detection value limit. The detection value limit threshold is set high enough such that noise that may be present under no-load conditions does not produce any samples within a given cycle that are recognized as current-spikes. The minimum count threshold is set high enough to accommodate normal operating conditions in which current-spikes may be expected to be present. For example, thyristor based light-dimmers will produce at least two current-spikes during each cycle as they switch on during both the positive and negative halves of the full 60-Hz cycle. A reliable determination of the presence of arcing within a given cycle may then be made through the proper adjustment of both the detection value limit and minimum count thresholds.

The components of the illustrative devices, systems and methods employed in accordance with the illustrated embodiments of the present invention, for example, as illustrated in FIGS. 1, 2A1, 2A2, 2A3, 2B1, 2B2, and 2B3, can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers. Examples of the computer-readable recording medium include, but are not limited to, read-only memory (ROM), random-access memory (RAM), CD-ROMs, magnetic tapes, floppy disks, optical data storage devices. It is envisioned that aspects of the present invention can be embodied as carrier waves (such as data transmission through the Internet via wired or wireless transmission paths). A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. The computer-readable recording medium can also be distributed over network-coupled computer systems so that the computer-readable code is stored and executed in a distributed fashion. Also, functional programs, codes, and code segments for accomplishing the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Method steps can also be performed by, and apparatus of the invention can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The above-presented description and figures are intended by way of example only and are not intended to limit the present invention in any way except as set forth in the following claims. It is particularly noted that persons skilled in the art can readily combine the various technical aspects of the various elements of the various exemplary embodiments that have been described above in numerous other ways, all of which are considered to be within the scope of the invention.

The above-described exemplary embodiments of an apparatus, system and method in computer-readable media include program instructions to implement various operations embodied by a computer. The media may also include, alone or in combination with the program instructions, data files, data structures, and the like. The media and program instructions may be those specially designed and constructed for the purposes of the present invention, or they may be of the kind well-known and available to those having skill in the computer software arts. Examples of computer-readable media include magnetic media such as hard disks, floppy disks, and magnetic tape; optical media such as CD ROM disks and DVD; magneto-optical media such as optical disks; and hardware devices that are specially configured to store and perform program instructions, such as read-only memory (ROM), random access memory (RAM), flash memory, and the like. The media may also be a transmission medium such as optical or metallic lines, wave guides, and so on, and is envisioned include a carrier wave transmitting signals specifying the program instructions, data structures, and so on. The computer-readable recording medium can also be distributed over network-coupled computer systems so that the computer-readable code is stored and executed in a distributed fashion. Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention.

Although exemplary embodiments of the present invention have been disclosed for illustrative purposes, those skilled in the art will appreciate that various modifications, additions, and substitutions are possible, without departing from the scope of the present invention. Therefore, the present invention is not limited to the above-described embodiments, but is defined by the following claims, along with their full scope of equivalents.

We claim:

1. A method of detecting and identifying arcing in an arc fault circuit interrupter having a power-line monitoring and processing circuit comprising:
   obtaining by the power-line monitoring and processing circuit first data indicative of a line current for a first cycle of a voltage waveform;
   obtaining by the power-line monitoring and processing circuit second data indicative of the line current for a second cycle of the voltage waveform subsequent to the first cycle;
   correlating by a second correlation estimator the second data with data representative of at least one known arc reference cycle;
   comparing by a first threshold comparator circuit an output of the second correlation estimator with an arc-event correlation threshold;
   correlating by a first correlation estimator the first data with the second data;
   comparing by a second threshold comparator circuit an output of the first correlation estimator with a previous-cycle correlation threshold; and
   outputting a signal indicative of an arc-event present during the second cycle of the voltage waveform when an output of the first threshold comparator circuit is indicative of the second data correlating with the at least one known arc reference cycle within the arc-event correlation threshold, and
   an output of the second threshold comparator circuit is indicative of the first data not correlating with the second data within the previous-cycle correlation threshold.

2. The method of detecting and identifying arcing of claim 1, wherein the first and second cycles of the line voltage and the line current are determined with reference to zero-crossings detected by a zero-crossing detector circuit on a rising edge of the voltage waveform indicative of a beginning of each cycle for the line current.

3. The method of detecting and identifying arcing of claim 1, further comprising collecting the obtained data indicative of the line current during each cycle of a plurality of cycles to estimate by one or more comparator circuit the likelihood of the presence of an arc-event within each individual cycle of the plurality of cycles,
   wherein an arc-fault is determined to be present when a pre-defined number of the arc-events are detected within a pre-defined number of contiguous cycles.

4. The method of detecting and identifying arcing of claim 1, wherein the at least one known arc reference cycle is based on measured current during arc events generated in a controlled fashion, the known arc reference cycle comprising the normalized average expected wave-shape of a single cycle of current in which an arc is present.

5. The method of detecting and identifying arcing of claim 1, wherein the arc-event correlation thresholds for gauging a degree of the correlation required for the detecting of the arc-event are based upon a determination of monotonic behavior in a root-means-square (RMS) amplitude of the line-current waveform over a pre-determined number of cycles.

6. The method of detecting and identifying arcing of claim 1, wherein the determining of the arc-fault further comprises determining when a pre-defined number of arc-events occur within a pre-defined number of contiguous cycles.

7. The method of detecting and identifying arcing of claim 6, wherein the required number of the detected arc-events and the pre-defined number of cycles in an observation window are determined based on a range classification of a root-means-square (RMS) amplitude of each observed cycle of the line-current.

8. The method of detecting and identifying arcing of claim 7, wherein the range classifications for arc test clearing times based on the current level being tested meet UL1699 for the class of the circuit interrupter.

9. The method of detecting and identifying arcing of claim 1, wherein:
   the first data is indicative of the line voltage and the line current for at least a portion of the first cycle of the voltage waveform;
   the second data is indicative of the line voltage and the line current for at least a portion of the second cycle of the voltage waveform subsequent to the first cycle and corresponding to the portion of the first cycle; and
   the data representative of the at least one known arc reference cycle is a portion of the at least one known arc reference cycle corresponding to the portion of the second cycle.

10. A system for detecting and identifying arcing in an arc fault circuit interrupter having a power-line monitoring and processing circuit comprising:
    power-line monitoring and processing circuit obtaining data indicative of line voltage and line current; and
    a logic circuitry including non-transitory computer-readable medium storing computer readable instructions and one or more processors coupled to said non-transitory computer readable medium, and when executing said computer readable instructions said logic circuitry:

controls said power-line monitoring and processing circuit to obtain a first data indicative of the line voltage and the line current for a first cycle of the voltage waveform;

controls said power-line monitoring and processing circuit to obtain a second data indicative of the line voltage and the line current for a second cycle of the voltage waveform subsequent to the first cycle;

correlates the second data with the data representative of at least one known arc reference cycle;

correlates the first data stored with the second data; and outputs a signal indicative of an arc-event present during the second cycle when the second data correlates with the at least one known arc reference cycle within an arc-event correlation threshold, and the first data does not correlate with the second data within a previous-cycle correlation threshold.

11. The system of claim 10, wherein:

power-line monitoring and processing circuit comprises a sensor coil connected to the line voltage and line current; and at least one of the processors comprises analog electronics, wherein the sensed current is converted to a conditioned signal prior to input via an analog to digital converter to at least one of the processors.

12. The system of claim 11, wherein the analog electronics comprise a band-pass filter, an integrator circuit and a scaling circuit for processing the line current.

13. The system of claim 10, wherein when executing said computer readable instructions said logic circuitry:

sets the arc-event correlation thresholds for gauging a degree of the correlation required for the detecting of the arc-event based upon a determination of monotonic behavior in a root-mean-square (RMS) amplitude of the line current waveform over a pre-determined number of cycles.

14. The system of claim 13, wherein when executing said computer readable instructions said logic circuitry:

determines when a pre-defined number of arc-events occur within a pre-defined number of contiguous cycles.

15. The system of claim 14, wherein the required number of the detected arc-events and the pre-defined number of cycles in an observation window are determined based on a range classification of the RMS amplitude of each observed cycle of the line-current.

16. The system of claim 15, wherein the range classifications for arc test clearing times based on the current level being tested meet UL1699 for the class of the circuit interrupter.

* * * * *